US005863519A

United States Patent [19]
Golman et al.

[11] Patent Number: 5,863,519
[45] Date of Patent: *Jan. 26, 1999

[54] COMPOSITION AND METHOD OF MRI USING BOTH A POSITIVE AND A NEGATIVE CONTRAST AGENT

[75] Inventors: Klaes Golman, Rungsted Kyst, Denmark; Göran Pettersson, Hjärup, Sweden; Arne Berg, Blommenholm, Norway; Jo Klaveness, Oslo, Norway; Pål Rongved, Nesoddtangen, Norway; Peter Leander, Lund, Sweden; Ib Leunbach, Dragör, Denmark; Wolfgang Günther, West Chester, Pa.

[73] Assignee: Nycomed Imaging AS, Oslo, Norway

[*] Notice: This patent issued on a continued prosecution application filed under 37 CFR 1.53(d), and is subject to the twenty year patent term provisions of 35 U.S.C. 154(a)(2).

[21] Appl. No.: 602,289

[22] Filed: Feb. 16, 1996

Related U.S. Application Data

[63] Continuation-in-part of Ser. No. 462,873, Jun. 5, 1995, abandoned, and Ser. No. 465,100, Jun. 5, 1995, Pat. No. 5,716,598.

[30] Foreign Application Priority Data

Aug. 18, 1994 [GB] United Kingdom .................. 9416767
Aug. 18, 1994 [GB] United Kingdom .................. 9416768

[51] Int. Cl.⁶ .................................................. A61B 5/055
[52] U.S. Cl. ............................................. 424/9.36; 424/9.3
[58] Field of Search ............................... 424/9.32, 9.322, 424/9.36, 9.3, 9.363, 9.361, 9.364; 128/653.4; 600/410

[56] References Cited

U.S. PATENT DOCUMENTS

| | | |
|---|---|---|
| 4,804,529 | 2/1989 | Bardy et al. . |
| 4,826,673 | 5/1989 | Dean et al. . |
| 4,859,451 | 8/1989 | Quay et al. . |
| 4,963,344 | 10/1990 | Gries et al. . |
| 5,128,121 | 7/1992 | Berg et al. . |
| 5,143,716 | 9/1992 | Unger .................................. 424/9.322 |
| 5,250,285 | 10/1993 | Lauffer et al. . |
| 5,290,537 | 3/1994 | Moore et al. . |
| 5,292,729 | 3/1994 | Ashmead . |
| 5,314,680 | 5/1994 | Rajagopalan et al. . |
| 5,314,681 | 5/1994 | Leunbach et al. .......................... 424/9 |
| 5,439,668 | 8/1995 | Almen et al. . |

FOREIGN PATENT DOCUMENTS

| | | |
|---|---|---|
| 0 401 096 | 12/1990 | European Pat. Off. . |
| 0 524 633 | 1/1993 | European Pat. Off. . |
| 87/04622 | 8/1987 | WIPO . |
| 8911874 | 12/1989 | WIPO ............................. A61K 49/00 |
| 93/06811 | 4/1993 | WIPO . |

OTHER PUBLICATIONS

Johnson et al., *Proc. Soc. Exp. Biol. Med.,* 199(4), 470–480, 1992.
Seaborn et al., *Biol. Trace Elem. Res.,* 41(3), 279–294, Jun. 1994.
Bell et al., *J. Toxicol. Environ. Health,* 26(4), 387–398, 1989.
Giurgea et al., *Stud. Cercet. Biol. Ser. Biol. Anim.,* 44(2), 135–137, 1992.
Lonnerdal, *J. Nutr.,* 119(12), 1839–1844; discussion 1845, 1989.
Gerard et al., *Bull. Soc. Chim. Fr.,* No. 11–12, Pt. 1, 2404–2408, 1975.
Gerard, *Bull. Soc. Chim. Fr.,* No. 11–12, 451–456, 1979.
Rubin et al., *Magn. Reson. Med.,* 23(1), 154–165, 1992.
Stampfli et al., *J. Coord. Chem.,* 1(3), 173–177, 1972.
Petrola, *Finn. Chem. Lett.,* 13(5), 129–135, 1986.

*Primary Examiner*—José G. Dees
*Assistant Examiner*—Michael G. Hartley
*Attorney, Agent, or Firm*—Bacon & Thomas

[57] ABSTRACT

There is provided a contrast medium composition comprising: (a) a first contrast agent comprising a physiologically tolerable manganese compound together with an uptake promoter, having a manganese concentration of at least 0.3 mM or being in a dosage unit form containing at least 300 μmol manganese, wherein the uptake promoter comprises a physiologically tolerable reducing compound containing an α-hydroxy ketone group or a physiologically tolerable acid containing α- and/or β- hydroxy or amino groups, or a salt thereof, and/or vitamin D; together with (b) a second contrast agent.

Such compositions are particularly suitable for imaging of the liver.

17 Claims, 18 Drawing Sheets

COMPOSITION AND METHOD OF MRI USING BOTH A POSITIVE AND A NEGATIVE CONTRAST AGENT

This is a continuation-in-part of U.S. patent application Ser. No. 08/462,873 filed Jun. 5, 1995, now abandoned, and U.S. patent application Ser. No. 08/465,100 filed Jun. 5, 1995, now U.S. Pat. No. 5,716,598.

FIELD OF THE INVENTION

The present invention relates to improvements in and relating to magnetic resonance imaging (MRI) and in particular to compositions for use as or in the preparation of MRI contrast media for imaging of the stomach, intestine, liver, bile duct and gall bladder.

BACKGROUND OF THE INVENTION

MRI is now well established as a medical diagnostic tool. The ability of the technique to generate high quality images and to differentiate between soft tissues without requiring the patient to be exposed to ionizing radiation has contributed to this success.

Although MRI can be performed without using added contrast media, it has been found that substances which affect the nuclear spin reequilibration of the nuclei (hereinafter the "imaging nuclei"—generally water protons in body fluids and tissues) responsible for the magnetic resonance (MR) signals from which the images are generated may be used to enhance image contrast and accordingly, in recent years, many such materials have been suggested as MRI contrast agents.

The enhanced contrast obtained with the use of contrast agents enables particular organs or tissues to be visualized more clearly by increasing or by decreasing the signal level of the particular organ or tissue relative to that of its surroundings. Contrast agents raising the signal level of the target site relative to that of its surroundings are termed "positive" contrast agents whilst those lowering the signal level relative to surroundings are termed "negative" contrast agents.

The majority of materials now being proposed as MRI contrast media achieve a contrast effect because they contain paramagnetic, superparamagnetic or ferromagnetic species.

For ferromagnetic and superparamagnetic contrast agents, which are negative MRI contrast agents, the enhanced image contrast derives primarily from the reduction in the spin reequilibration parameter known as $T_2$ or as the spin-spin relaxation time, a reduction arising from the effect on the imaging nuclei of the fields generated by the ferromagnetic or superparamagnetic particles.

Paramagnetic contrast agents on the other hand may be either positive or negative MRI contrast agents. The effect of paramagnetic substances on magnetic resonance signal intensities is dependent on many factors, the most important of which are the concentration of the paramagnetic substance at the imaged site, the nature of the paramagnetic substance itself and the pulse sequence and magnetic field strength used in the imaging routine. Generally, however, paramagnetic contrast agents are positive MRI contrast agents at low concentrations where their $T_1$ lowering effect dominates and negative MRI contrast agents at higher concentrations where their $T_2$ lowering effect is dominant. In either event, the relaxation time reduction results from the effect on the imaging nuclei of the magnetic fields generated by the paramagnetic centres.

The use of paramagnetic, ferromagnetic and superparamagnetic materials as MRI contrast agents has been widely advocated and broad ranges of suitable materials have been suggested in the literature.

An example of a physiologically tolerable paramagnetic material known for use as an MRI contrast agent is manganese ion, which may conveniently be used in the form of its salts or chelates. Indeed, even at very low i.v. dosages (about 5–10 µmol/kg bodyweight) manganese has been found to be particularly effective as a contrast agent for imaging of the liver.

However manganese, when administered intravenously as a contrast agent, may be teratogenic at clinical dosages. Administered intravenously, manganese is also known to interfere with the normal functioning of the heart by replacement of calcium in the calcium pump of the heart.

In order to reduce the direct effect on the heart, oral administration has been proposed. This ensures passage of the contrast agent through the liver before going to the heart.

Oral administration of $MnCl_2$ as a liver imaging MR contrast agent has been proposed and orally administered $MnCl_2$ has not been found to be teratogenic. However, the absorption of $MnCl_2$ through the gut is poor, and as a result the dosage required for clinical efficacy is of the order of 100–1000 µmol/kg bodyweight. In the event of damage to the gut resulting in increased uptake, such a high dosage level still has the potential for causing undesired adverse effects, eg. cardiac effects.

SUMMARY OF THE INVENTION

We have now surprisingly found that gastrointestinal tract manganese contrast agents suitable for imaging of the liver may be produced by the incorporation of an uptake promoter capable of enhancing manganese transport across the membranes of the g.i. tract.

Compounds which have been found to be suitable for use as uptake promoters include reducing compounds containing an α-hydroxy ketone group (—C(OH)—CO—), acids containing α- and/or β-hydroxy or amino groups, as well as vitamin D.

Thus, viewed from one aspect the present invention provides a contrast medium composition comprising a physiologically tolerable manganese compound, an uptake promoter and a physiologically tolerable carrier or excipient, having a manganese concentration of at least 0.3 mM or being in a dosage unit form containing at least 300 µmol manganese, wherein the uptake promoter comprises a physiologically tolerable reducing compound containing an α-hydroxy ketone group, a physiologically tolerable acid containing α- and/or β-hydroxy or amino groups, or a salt thereof, and/or vitamin D.

As used herein, the expression "acid containing α- and/or β-hydroxy or amino groups" is intended to include aromatic acids containing ortho-hydroxy or ortho-amino groups.

Viewed from a further aspect the present invention provides a method of generating a magnetic resonance image of a human or non-human, preferably mammalian, animal body which method comprises administering into the gastrointestinal tract of a said body a contrast medium comprising a physiologically tolerable manganese compound and a physiologically tolerable reducing compound containing an α-hydroxy ketone group or a physiologically tolerable acid containing α- and/or β-hydroxy or amino groups, or a salt thereof, and/or vitamin D, and generating a magnetic resonance image of the liver and the gastro-intestinal tract of said body.

Viewed from a yet further aspect the invention also provides a method of generating a magnetic resonance image of a human or non-human animal body, which method comprises administering into the gastrointestinal tract of a said body an effective amount of a composition comprising: (a) a first contrast agent comprising a physiologically tolerable manganese compound, a physiologically tolerable reducing compound containing an α-hydroxy ketone group or a physiologically tolerable acid containing α- and/or β-hydroxy or amino groups, or a salt thereof, and/or vitamin D, preferably having a manganese concentration of at least 0.3 mM or being in a dosage unit form containing at least 300 μmol manganese, together with (b) a second contrast agent and generating a magnetic resonance image of the liver and abdomen of said body.

In a further aspect the invention also provides an MRI contrast agent kit comprising in a first container a physiologically tolerable manganese compound, and in a second container a physiologically tolerable reducing compound containing an α-hydroxy ketone group or a physiologically tolerable acid containing α- and/or β-hydroxy or amino groups, or a salt thereof, and/or vitamin D.

Viewed from a further aspect the invention also provides an MRI contrast agent kit comprising in a first container a first contrast agent comprising a physiologically tolerable manganese compound, a physiologically tolerable reducing compound containing an α-hydroxy ketone group or a physiologically tolerable acid containing α- and/or β-hydroxy or amino groups, or a salt thereof, and/or vitamin D, preferably having a manganese concentration of at least 0.3 mM or being in a dosage unit form containing at least 300 μmol manganese, and in a second container a second contrast agent comprising a particulate ferromagnetic or superparamagnetic material or Gd or Dy ions bound to a polymeric matrix.

DETAILED DESCRIPTION

The contrast medium composition according to the invention may comprise a manganese compound together with a mixture of several uptake promoters.

The manganese compound, which preferably is soluble in gastrointestinal fluid may for example be a chelate or a salt, or may be a mixture of different salts and/or chelates. Particularly preferred are metal chelates and salts in which the manganese is present as Mn(II) rather than Mn(III) since the former has a higher magnetic moment and thus is more effective as an MR contrast agent.

The reducing nature of the uptake promoter is important since normal uptake of manganese by the gut tends to favour Mn(II) rather than Mn(III).

Preferred compositions according to the invention are those in which the reducing compound further contains an oxygen atom in a heterocyclic ring structure.

Particularly preferred as an uptake promoter in the compositions of the invention is ascorbic acid which has been found to increase the uptake of manganese in the liver about 5-fold compared with oral administration of $MnCl_2$ alone, This surprising increase is demonstrated in FIG. 2 of the accompanying drawings. Moreover ascorbic acid (vitamin C) is particularly preferred as an uptake promoter since it is cheap, readily available and particularly well tolerated by the body.

Yet more particularly preferred compositions in accordance with the invention are those in which the uptake promoter is kojic acid. The dramatic increase in the uptake of manganese in the liver following administration of $MnCl_2$+kojic acid can be seen from FIG. 5 of the accompanying drawings.

Examples of acids which have been found to be particularly effective as uptake promoters in the compositions of the invention include carboxylic acids, e.g. gluconic and salicyclic acid. The effect of the addition of salicylic acid to $MnCl_2$ on MRI enhancement of the liver can be seen in FIG. 8 of the accompanying drawings. α- and β- amino acids have also been found to be useful as uptake promoters, in particular α-amino acids, e.g. glycine, valine, glutamine, aspartic acid, glutamic acid, lysine, arginine, cysteine and methionine, especially arginine, lysine and aspartic acid. The effect of addition of various α-amino acids to $MnCl_2$ on MRI enhancement of the liver is shown in accompanying FIG. 9.

Other preferred compositions in accordance with the invention are those which comprise vitamin D as an uptake promoter.

Using the compositions of the invention, the liver can be effectively MR imaged with a significant reduction in the dosage of manganese otherwise required. Thus, for example, a 50% enhancement of the liver can be obtained by oral administration of 100 μmol manganese/kg body weight and 1 mmol ascorbic acid/kg. Such a dosage results in the same degree of enhancement of the liver as 5 μmol Mn(II)/kg body weight ($MnCl_2$, i.v.) or as 500 μmol Mn(II)/kg body weight ($MnCl_2$, p.o.).

FIG. 1 hereto demonstrates the effect of p.o. administration of $MnCl_2$ and ascorbic acid on MR liver enhancement compared with p.o. administration of $MnCl_2$ alone.

Increase in the ratio of ascorbic acid to $MnCl_2$ results in an increase in the enhancement effect obtained. This dose-response relationship can be seen from FIG. 2 hereto.

The gradual increase in enhancement of the liver with time following administration of a composition in accordance with the invention enables the dynamics of uptake of the contrast agent by the liver to be monitored (see for example FIG. 2). This is of particular importance in enabling identification of areas of healthy tissue and areas of possible tumor growth.

In the compositions according to the invention, the preferred molar ratio of manganese to uptake promoter is from 1:0.2 to 1:50, eg. 1:1 to 1:20, especially 1:3 to 1:6, particular preferably about 1:5.

The uptake promoter may if desired be present in whole or in part as the counterion to the manganese ions. Thus in one embodiment the composition of the invention comprises as both manganese compound and uptake promoter a manganese salt of a reducing compound containing an α-hydroxy ketone group or a manganese salt of an acid containing α- and/or β- hydroxy or amino groups, eg. manganese (II) ascorbate or manganese salicylate.

The compositions according to the invention may be used to achieve a so-called "double contrast effect" by increasing the signal level from the liver whilst at the same time decreasing that from the surrounding tissues, in particular from the gut. Such an effect enables yet further enhancement of the liver.

A double contrast effect and margin definition can be achieved with the compositions of the invention since the resulting manganese ion concentration within the g.i. tract will generally be such as to create a signal suppressing effect there. In this case, to avoid image artefacts resulting from pockets of the gut being contrast agent free, it is desirable to incorporate in the compositions a viscosity enhancing agent and desirably also an osmoactive agent. Examples of suitable viscosity enhancers and osmoactive agents are described in WO 91/01147 and WO 91/01148.

In a particularly preferred embodiment, the compositions of the invention may be used in combination with a second contrast agent having either a positive or negative contrast effect. Preferably the compositions of the invention are used in combination with a second contrast agent having an opposing contrast effect. This results in a "double contrast effect" enabling visualisation and margin definition of the liver to be particularly enhanced.

As mentioned above, paramagnetic materials such as manganese ions may act as either positive or negative MRI contrast agents depending upon a number of factors, including the concentration of the ions at the imaging site and the magnetic field strength used in the imaging procedure. At the concentrations of manganese contemplated for use in the compositions of the invention, the manganese-containing contrast agent will, in general, function as a positive contrast agent. The second contrast agent is therefore conveniently a negative contrast agent and may be any negative MRI contrast agent suitable for oral administration. However, as indicated above, any MR contrast agent, negative or positive, may be used.

Examples of negative MRI contrast agents for use in combination with the compositions of the invention include known ferromagnetic and superparamagnetic species, such as for example magnetic iron oxide particles either free or enclosed within or bound to a non-magnetic matrix material such as a polysaccharide eg. LUMIREM and sulphonated polystyrene eg. ABDOSCAN®.

Further examples of contrast agents for use in combination with the compositions of the invention include Gd and Dy ions bound to a polymeric matrix, for example LUMIREM or GADOLITE (Gadolinium alumina silicate oral suspension).

When using the compositions of the invention to achieve a double contrast effect, it is particularly preferable to incorporate a viscosity enhancing agent which attains its full viscosity enhancing effect only after administration of the contrast medium. The contrast medium is thus able to be ingested in a relatively tolerable form while yet developing the desired viscosity at or during passage towards the site which is to be imaged.

The compositions of the invention are particularly suited to use, if required after dispersion in aqueous media, for imaging of the liver. For such a purpose the compositions may be administered into the gastrointestinal tract orally, rectally or via a stomach tube.

It is possible to formulate the contrast medium immediately or shortly prior to administration by mixing the uptake promoter with the manganese species.

The contrast agent compositions of the invention may of course include components other than the uptake promoter, the manganese compound, the viscosity enhancing and osmoactive agents, for example conventional pharmaceutical formulation aids such as wetting agents, buffers, disintegrants, binders, fillers, flavouring agents and liquid carrier media such as sterile water, water/ethanol etc.

For oral administration, the pH of the composition is preferably in the acid range, eg. 2 to 7 and while the uptake promoter may itself serve to yield a composition with this pH, buffers or pH adjusting agents may be used.

The contrast media may be formulated in conventional pharmaceutical administration forms, such as tablets, capsules, powders, solutions, dispersions, syrups, suppositories etc.

The preferred dosage of the composition according to the present invention will vary according to a number of factors, such as the administration route, the age, weight and species of the subject and the particular uptake promoter used. Conveniently, the dosage of manganese will be in the range of from 5 to 500 $\mu$mol/kg bodyweight, preferably from 5 to 150 $\mu$mol/kg bodyweight, more preferably from 10 to 100 $\mu$mol/kg bodyweight, while the dosage of the uptake promoter will be in the range of from 5 $\mu$mol to 1 mmol/kg bodyweight, preferably from 25 $\mu$mol to 0.5 mmol/kg bodyweight.

Preferred embodiments of the invention will now be described by reference to the following non-limiting Examples and the accompanying drawings, in which:

Figures 17A, 17B, 17C:
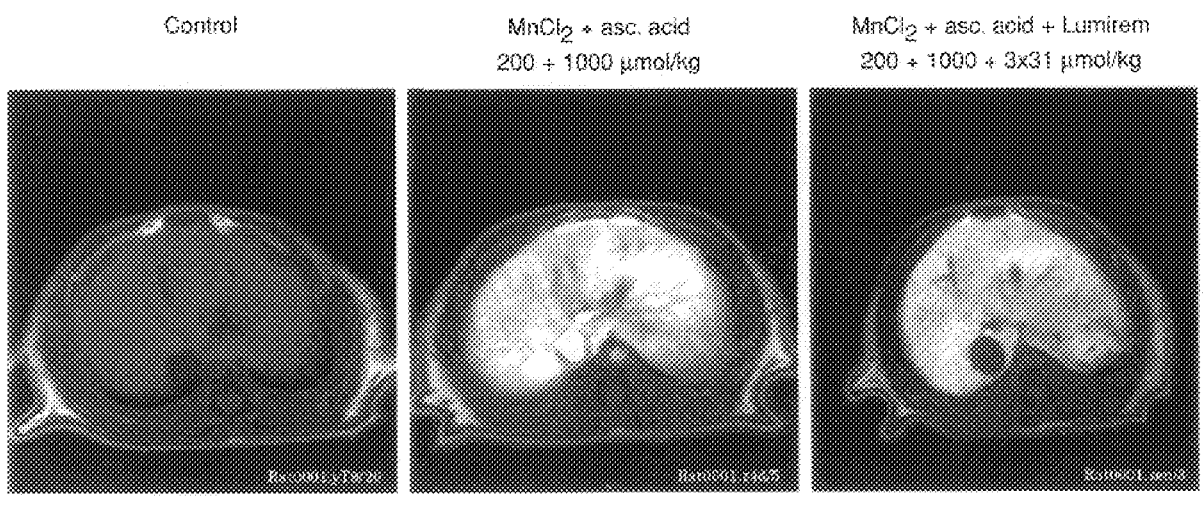
FIGS. 17 and 18 illustrate liver images from a control rat (A) and from rats following oral administration of 200 µmol/kg $MnCl_2$+1000 µmol/kg ascorbic acid (B) and oral administration of 200 µmol/kg $MnCl_2$+1000 µmol/kg ascorbic acid+3×31 µmol/kg LUMIREM (C).
Figures 18A, 18B, 18C:
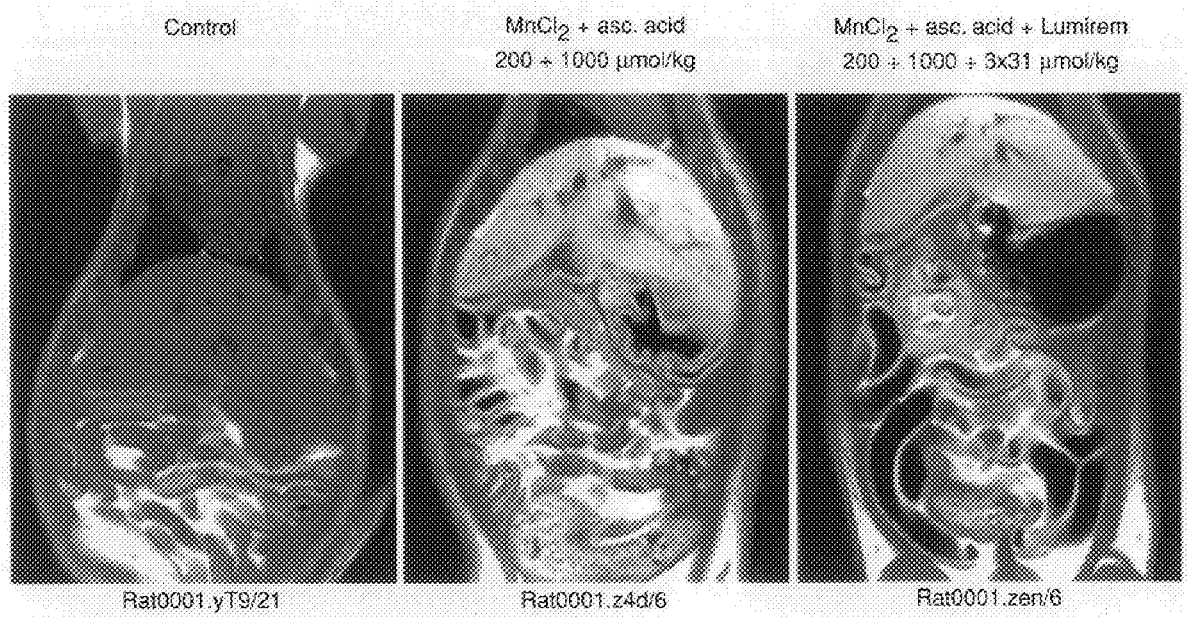

It is noted from FIGS. 17 and 18 that the addition of LUMIREM does not influence the signal intensity of the liver. However, addition of LUMIREM does noticeably reduce the signal intensity in the bowel lumen thereby enhancing visualisation of the liver.

For the measurement of the curves of FIGS. 1 to 9 the following materials were used:

FIG. 1

Mn-ascorbate

| | | |
|---|---|---|
| $MnCl_2 \times 2H_2O$ | | 6.48 g |
| Ascorbic acid | | 35.2 g |
| Water | ad | 1000 ml |

Mn-gluconate

| | | |
|---|---|---|
| Mn-gluconate | | 19.2 g |
| Water | ad | 1000 ml |

Mn-citrate

| | | |
|---|---|---|
| $MnCl_2 \times 2H_2O$ | | 6.48 g |
| $Na_3$-citrate $\times 2H_2O$ | | 23.5 g |
| Water | ad | 1000 ml |

FIG. 2

$MnCl_2$

| | | |
|---|---|---|
| $MnCl_2 \times 2H_2O$ | | 6.48 g |
| Water | ad | 1000 ml |

$MnCl_2$ + 0.1 mmol/kg ascorbic acid

| | | |
|---|---|---|
| $MnCl_2 \times 2H_2O$ | | 6.48 g |
| Ascorbic acid | | 3.52 g |
| Water | ad | 1000 ml |

$MnCl_2$ + 0.4 mmol/kg ascorbic acid

| | | |
|---|---|---|
| $MnCl_2 \times 2H_2O$ | | 6.48 g |
| Ascorbic acid | | 14.1 g |
| Water | ad | 1000 ml |

$MnCl_2$ + 1.0 mmol/kg ascorbic acid

| | | |
|---|---|---|
| $MnCl_2 \times 2H_2O$ | | 6.48 g |
| Ascorbic acid | | 3.52 g |
| Water | ad | 1000 ml |

$MnCl_2$ (0.2 mmol/kg) + ascorbic acid

| | | |
|---|---|---|
| $MnCl_2 \times 2H_2O$ | | 6.48 g |
| Ascorbic acid | | 3.52 g |
| Water | ad | 1000 ml |

$MnCl_2$ (0.5 mmol/kg) + ascorbic acid

| | | |
|---|---|---|
| $MnCl_2 \times 2H_2O$ | | 16.2 g |
| Ascorbic acid | | 3.52 g |
| Water | ad | 1000 ml |

$MnCl_2$ (2.0 mmol/kg) + ascorbic acid

| | | |
|---|---|---|
| $MnCl_2 \times 2H_2O$ | | 64.8 g |
| Ascorbic acid | | 3.52 g |
| Water | ad | 1000 ml |

FIG. 4

$MnCl_2$

| | | |
|---|---|---|
| $MnCl_2 \times 2H_2O$ | | 13.0 g |
| Water | ad | 1000 ml |

$MnCl_2$ + ascorbic acid − palmitate (0.4 mmol/kg)

| | | |
|---|---|---|
| L-ascorbic acid 6-palmitate | | 66.4 g |
| Polyethylene glycol 300 | ad | 1000 ml |

FIG. 5

$MnCl_2$ + kojic acid (0.4 mmol/kg)

| | | |
|---|---|---|
| $MnCl_2 \times 2H_2O$ | | 6.48 g |
| Kojic acid | | 11.4 g |
| Water | ad | 1000 ml |

FIG. 8

$MnCl_2$ (0.2 mmol/kg)

| | | |
|---|---|---|
| $MnCl_2 \times 2H_2O$ | | 6.48 g |
| Water | ad | 1000 ml |

$MnCl_2$ (0.2 mmol/kg) + ascorbic acid (0.4 mmol/kg)

| | | |
|---|---|---|
| $MnCl_2 \times 2H_2O$ | | 6.48 g |
| Ascorbic acid | | 14.1 g |
| Water | ad | 1000 ml |

$MnCl_2$ (0.2 mmol/kg) + salicylic acid (0.4 mmol/kg)

| | | |
|---|---|---|
| $MnCl_2 \times 2H_2O$ | | 6.48 g |
| Salicyclic acid sodium salt | | 12.8 g |
| Water | ad | 1000 ml |

FIG. 9

$MnCl_2$ (0.2 mmol/kg)

| | | |
|---|---|---|
| $MnCl_2 \times 2H_2O$ | | 6.48 g |
| Water | ad | 1000 ml |

$MnCl_2$ (0.2 mmol/kg) + ascorbic acid (0.4 mmol/kg)

| | | |
|---|---|---|
| $MnCl_2 \times 2H_2O$ | | 6.48 g |
| Ascorbic acid | | 14.1 g |
| Water | ad | 1000 ml |

$MnCl_2$ (0.2 mmol/kg) + glycine (0.4 mmol/kg)

| | | |
|---|---|---|
| $MnCl_2 \times 2H_2O$ | | 6.48 g |
| Glycine | | 7.76 g |
| Water | ad | 1000 ml |

$MnCl_2$ (0.2 mmol/kg) + valine (0.4 mmol/kg)

| | | |
|---|---|---|
| $MnCl_2 \times 2H_2O$ | | 6.48 g |
| Valine | | 9.36 g |
| Water | ad | 1000 ml |

$MnCl_2$ (0.2 mmol/kg) + glutamine (0.4 mmol/kg)

| | | |
|---|---|---|
| $MnCl_2 \times 2H_2O$ | | 6.48 g |
| Glutamine | | 11.7 g |
| Water | ad | 1000 ml |

$MnCl_2$ (0.2 mmol/kg) + aspartic acid (0.4 mmol/kg)

| | | |
|---|---|---|
| $MnCl_2 \times 2H_2O$ | | 6.48 g |
| Aspartic acid | | 13.8 g |
| Water | ad | 1000 ml |

$MnCl_2$ (0.2 mmol/kg) + glutamic acid (0.4 mmol/kg)

| | | |
|---|---|---|
| $MnCl_2 \times 2H_2O$ | | 6.48 g |
| Glutamic acid monosodium salt monohydrate | | 15.0 g |
| Water | ad | 1000 ml |

$MnCl_2$ (0.2 mmol/kg) + lysine (0.4 mmol/kg)

| | | |
|---|---|---|
| $MnCl_2 \times 2H_2O$ | | 6.48 g |
| Lysine monohydrochloride | | 14.6 g |
| Water | ad | 1000 ml |

-continued

| MnCl₂ (0.2 mmol/kg) + arginine (0.4 mmol/kg) | | |
|---|---|---|
| MnCl₂ × 2H₂O | | 6.48 g |
| Arginine monohydro-chloride | | 16.9 g |
| Water | ad | 1000 ml |

| MCl₂ (0.2 mmol/kg) + cysteine (0.4 mmol/kg) | | |
|---|---|---|
| MnCl₂ × 2H₂O | | 6.48 g |
| Cysteine monohydro-chloride monohydrate | | 14.0 g |
| Water | ad | 1000 ml |

| MnCl₂ (0.2 mmol/kg) + methionine (0.4 mmol/kg) | | |
|---|---|---|
| MnCl₂ × 2H₂O | | 6.48 g |
| Methionine | | 11.9 g |
| Water | ad | 1000 ml |

Figure 1:
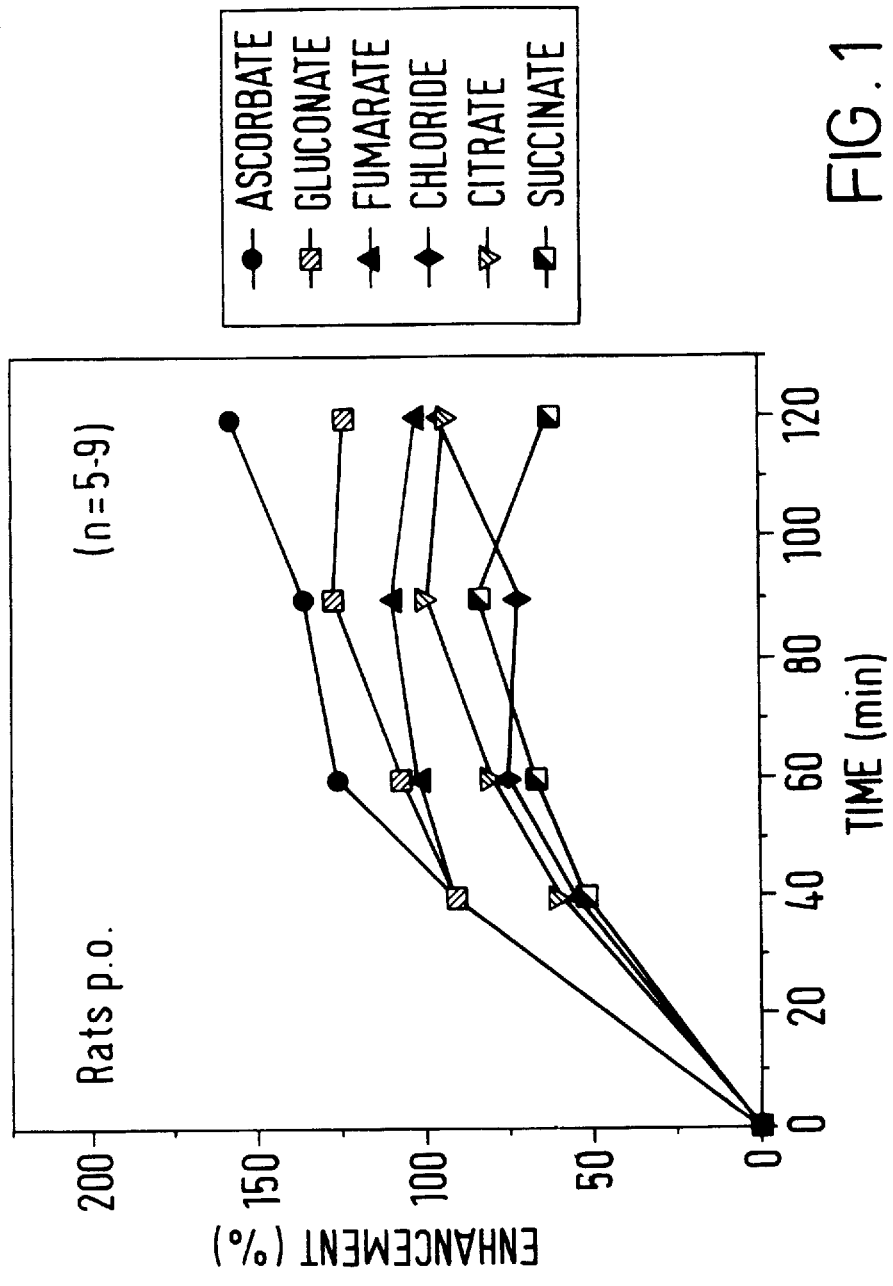
FIG. 1 is a graph illustrating the effect of p.o. administration of different $Mn^{2+}$ salts on liver enhancement.
Figure 2:
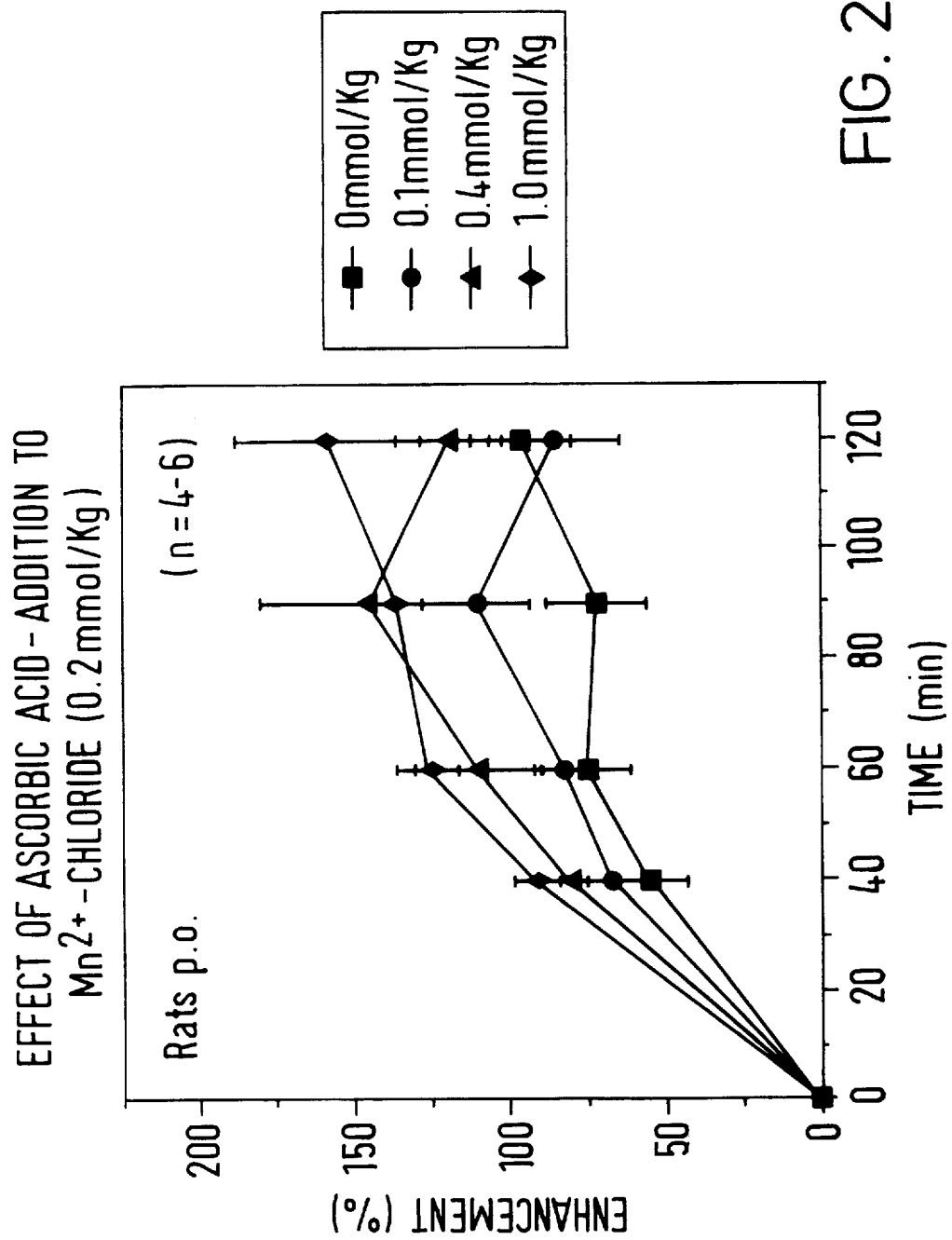
FIG. 2 is a graph illustrating the effect of p.o. administration of $MnCl_2$+ascorbic acid on liver enhancement at varying concentrations of ascorbic acid.
Figure 3:
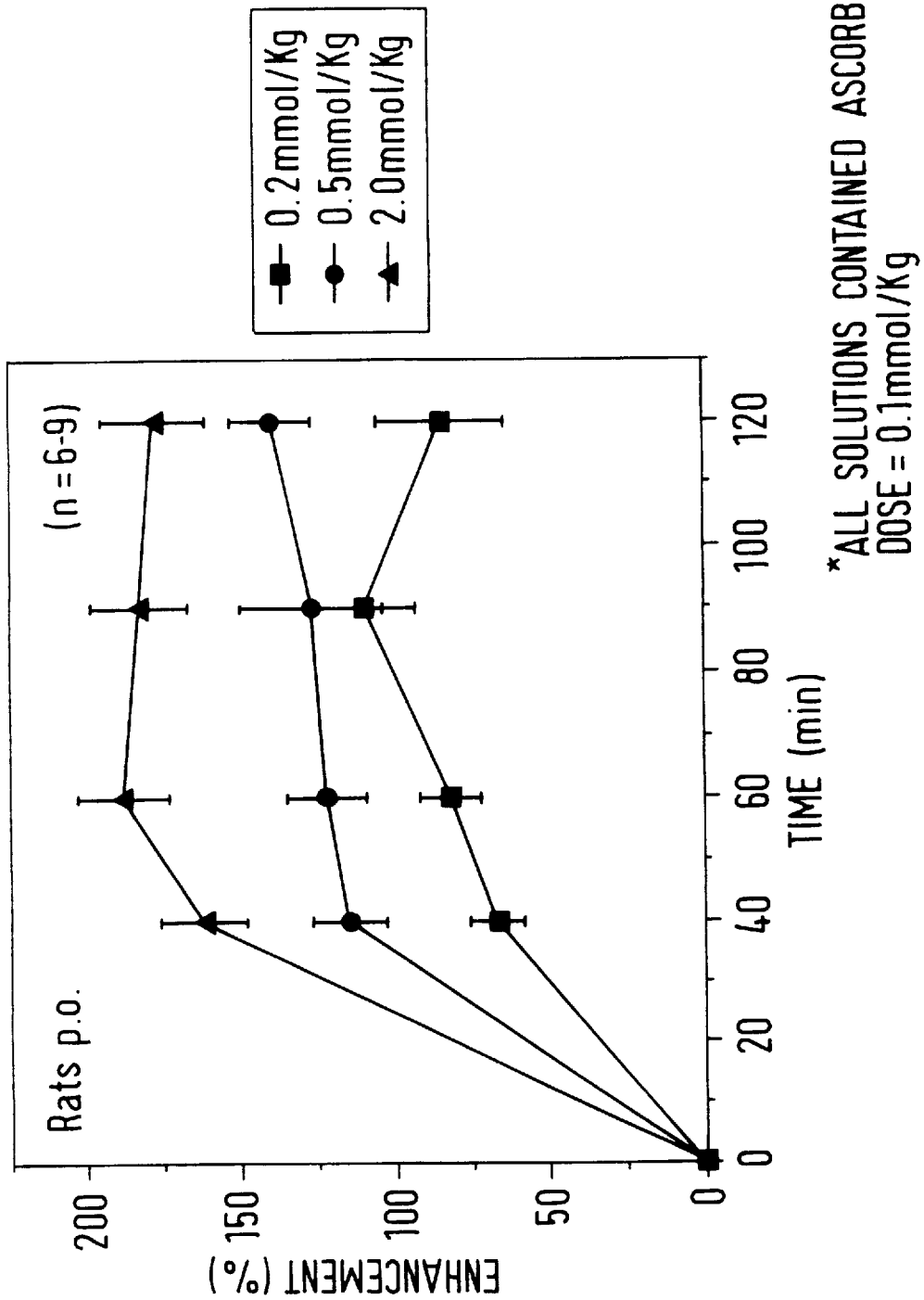
FIG. 3 is a graph illustrating the effect of p.o. administration of different doses of $MnCl_2$ containing 0.1 mmol/kg ascorbic acid on liver enhancement.
Figure 4:
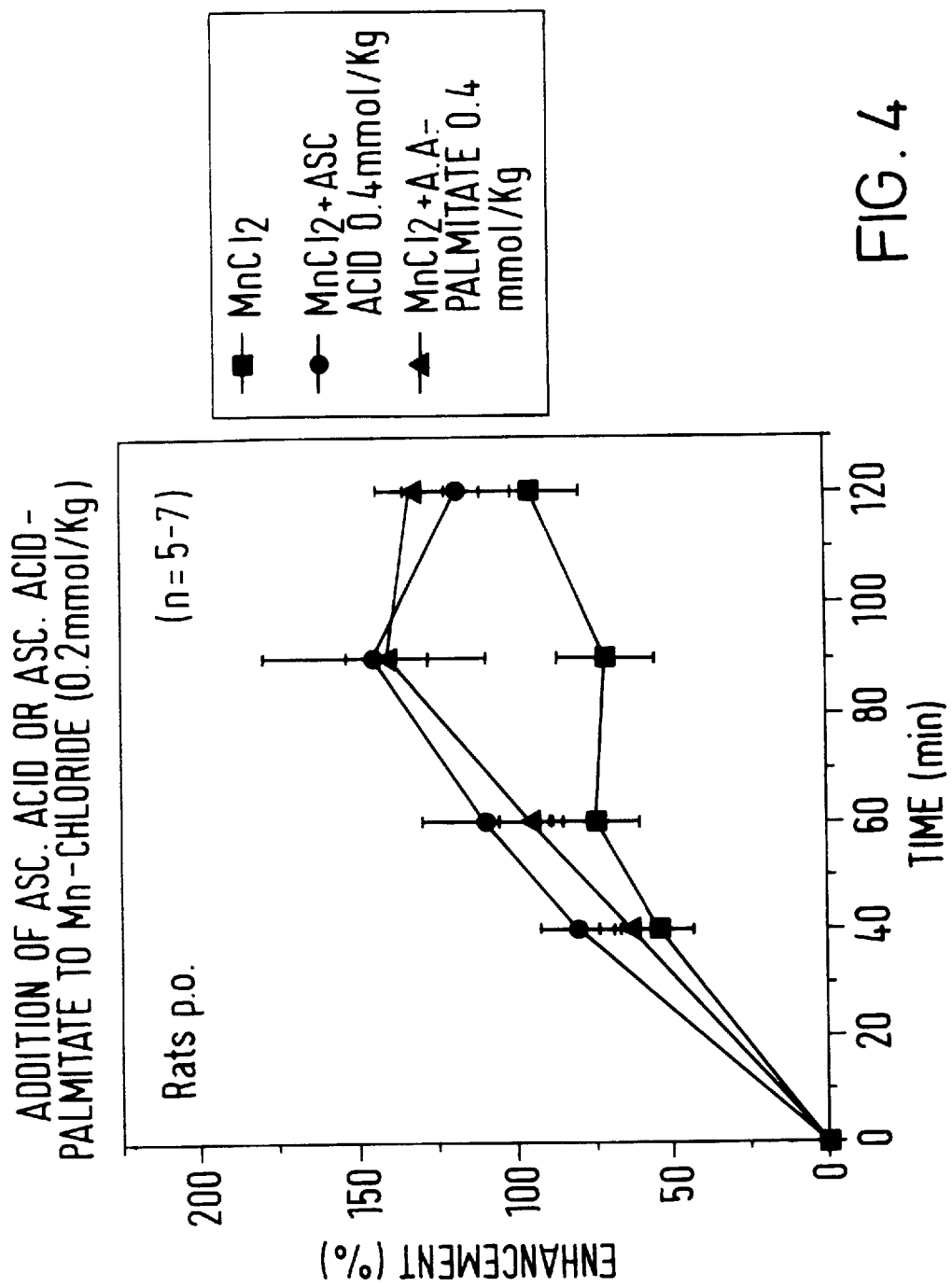
FIG. 4 is a graph illustrating the effect of the addition of ascorbic acid or ascorbic acid-palmitate to $MnCl_2$ on enhancement of the liver.
Figure 5:
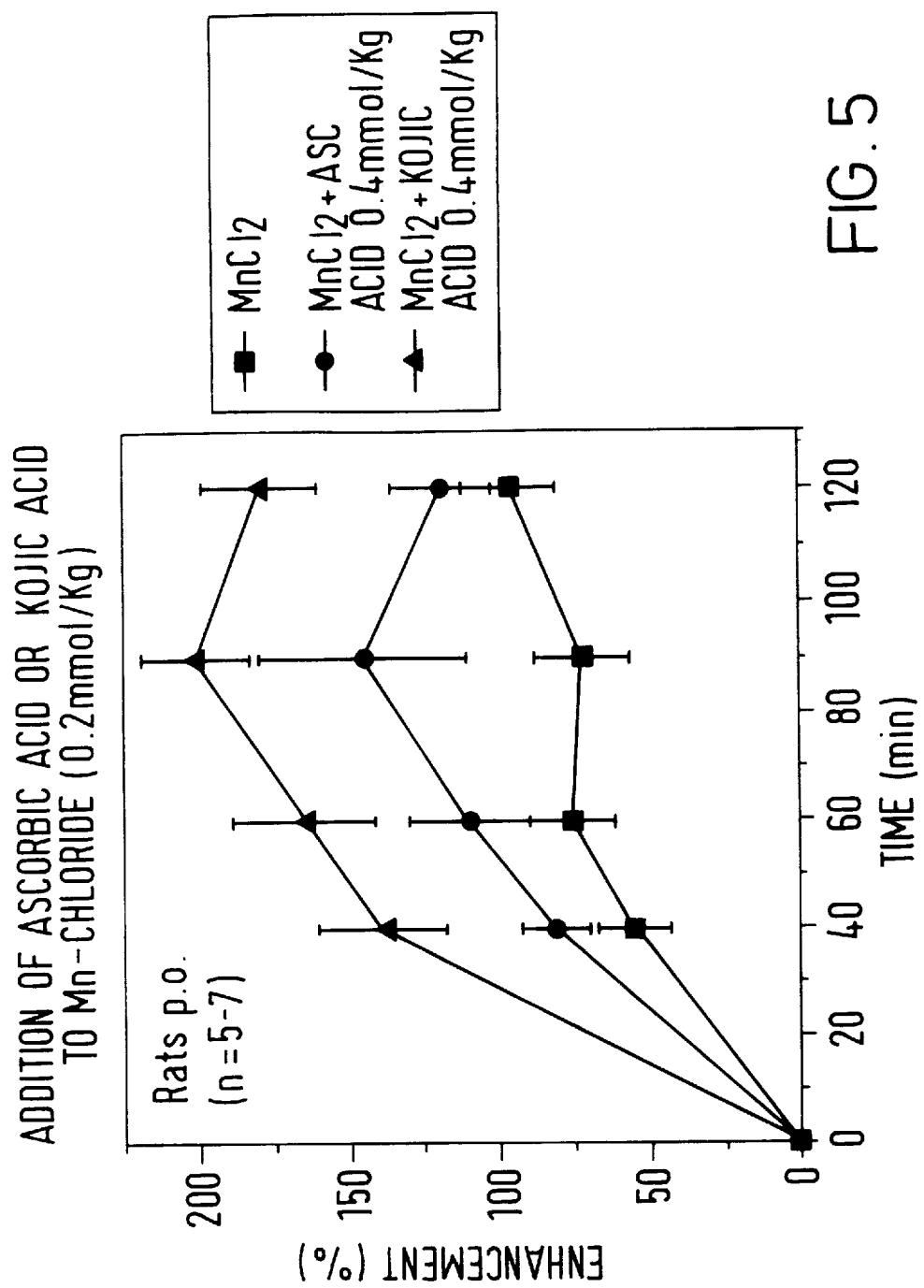
FIG. 5 is a graph illustrating the effect of the addition of ascorbic acid or kojic acid to $MnCl_2$ on enhancement of the liver.
Figure 6:
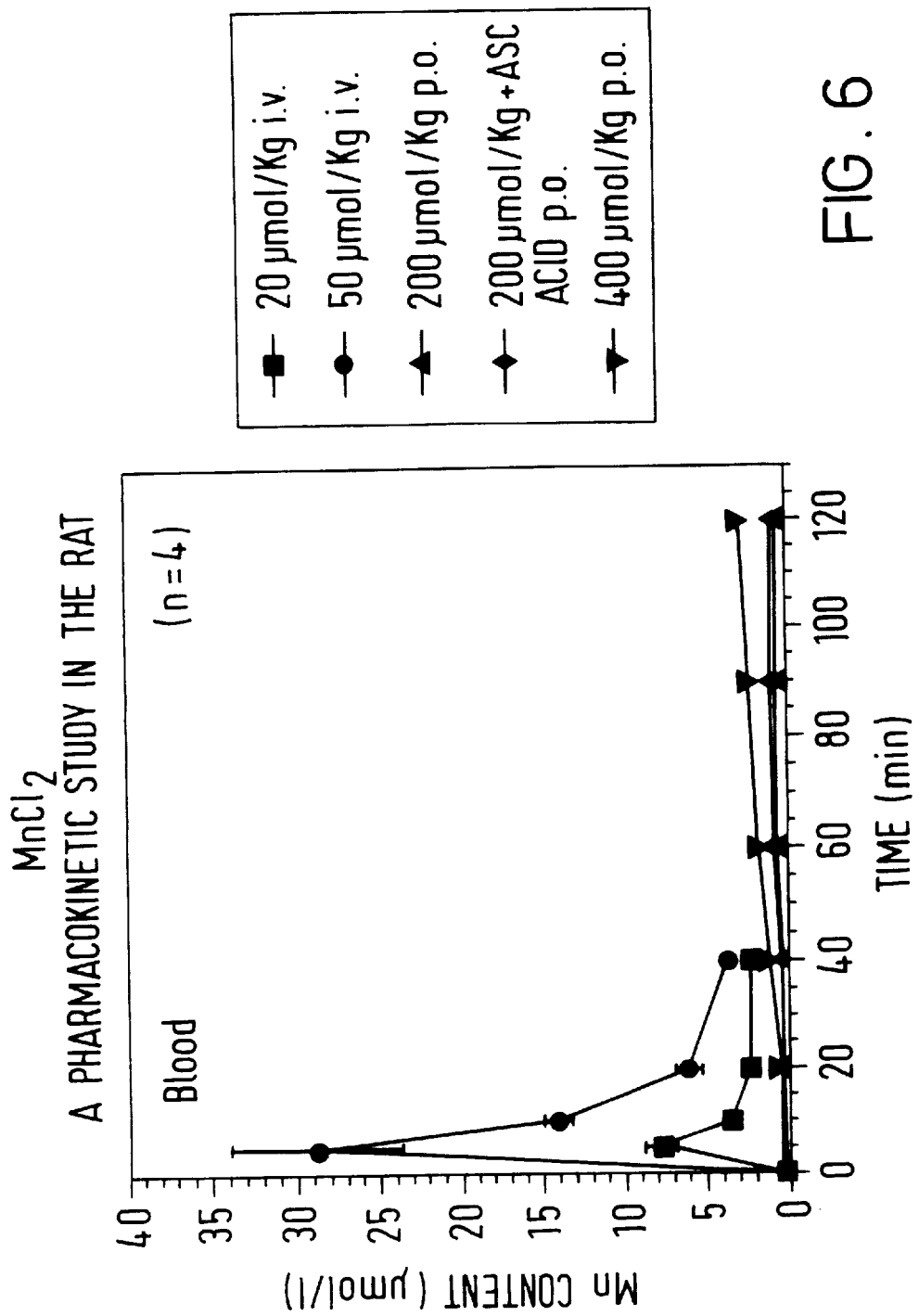
FIG. 6 is a graph illustrating the results of a pharmacokinetic study to determine the variation in concentration of Mn(II) in the blood following administration of various Mn(II)-containing compositions.
Figure 7:
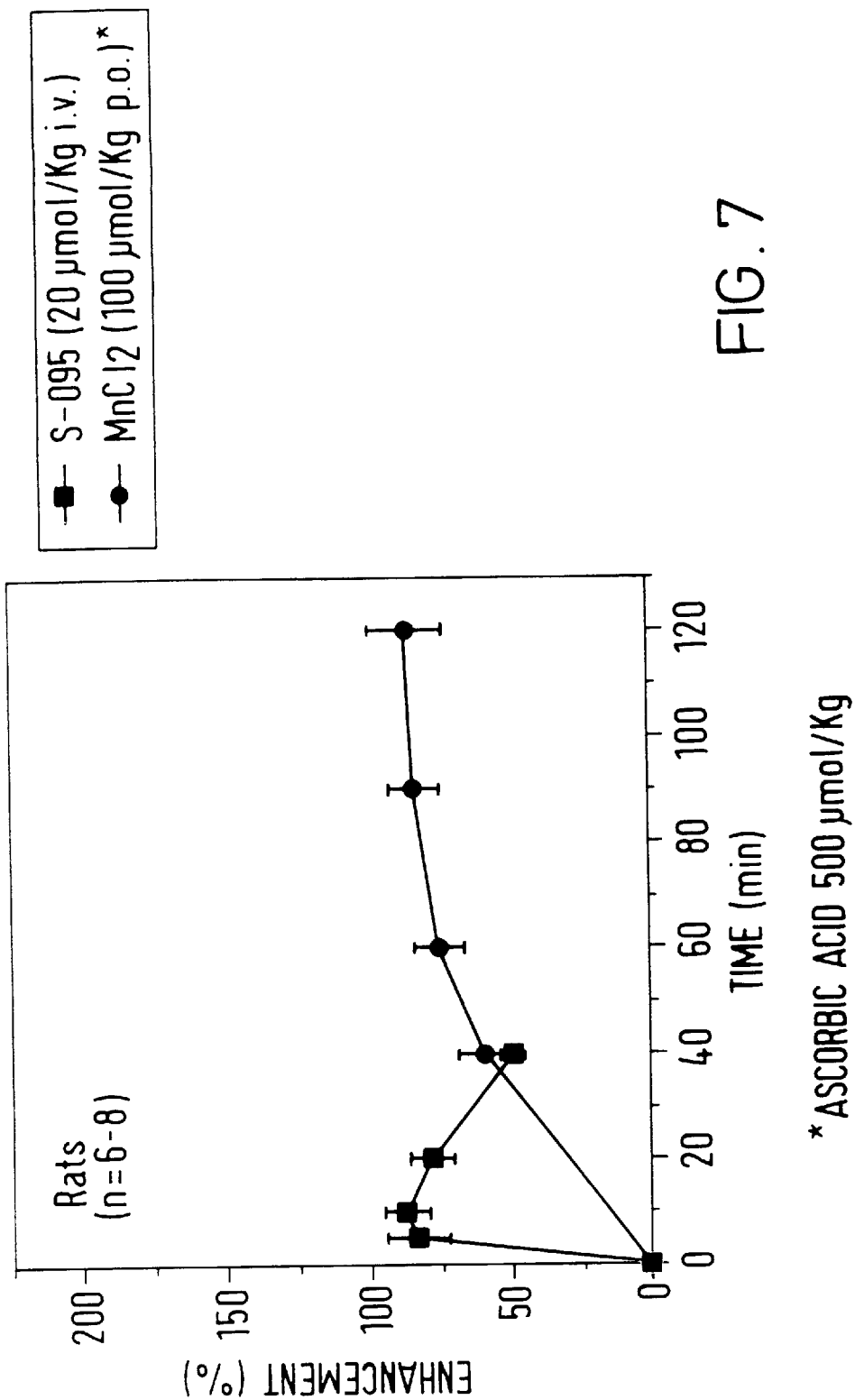
FIG. 7 is a graph comparing the effect on liver enhancement of i.v. administration of Mn DPDP (S-095) with that of p.o. administration of $MnCl_2$+ascorbic acid.
Figure 8:
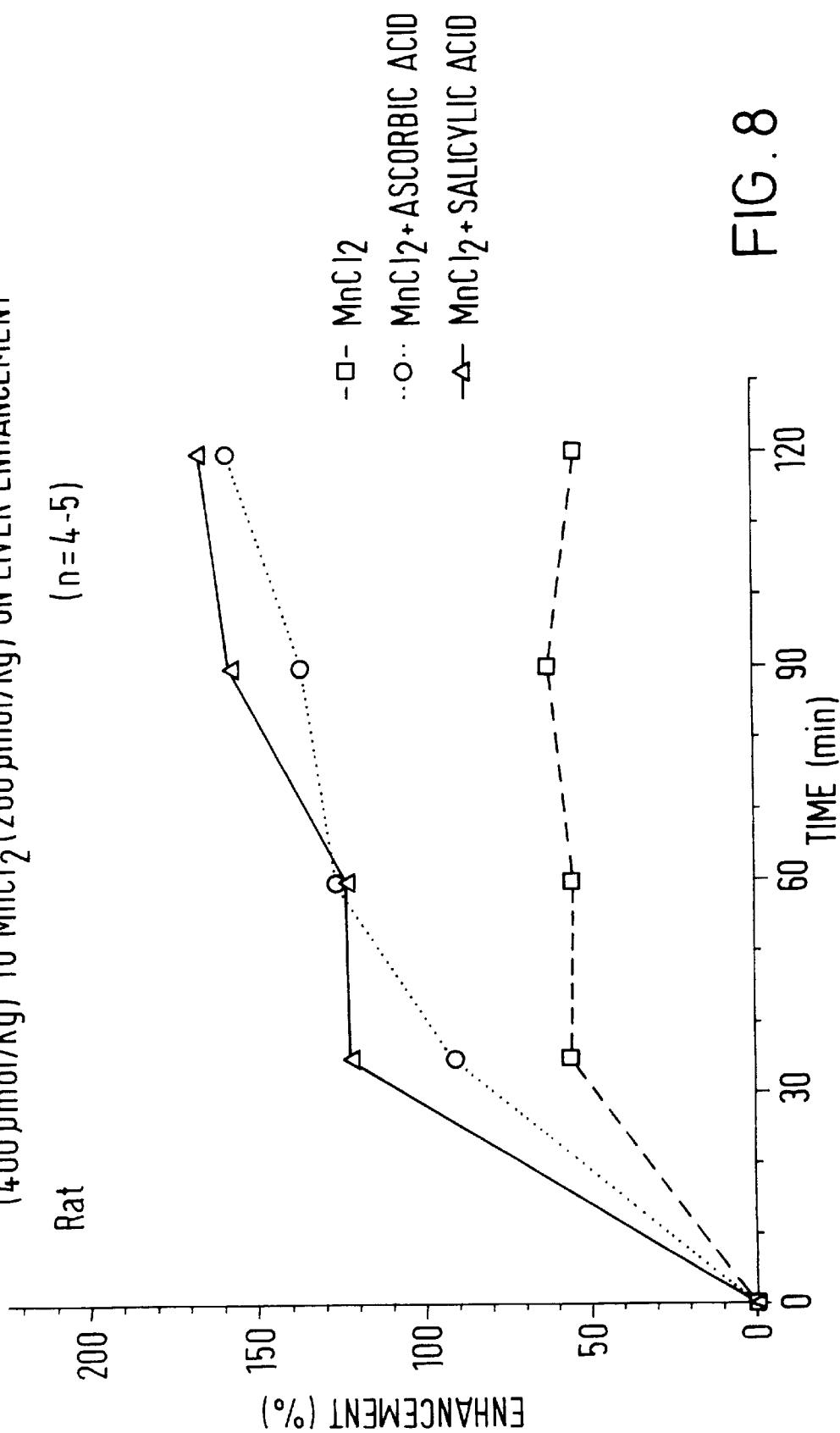
FIG. 8 is a graph illustrating the effect of the addition of ascorbic and salicylic acids to $MnCl_2$ on liver enhancement.
Figure 9:
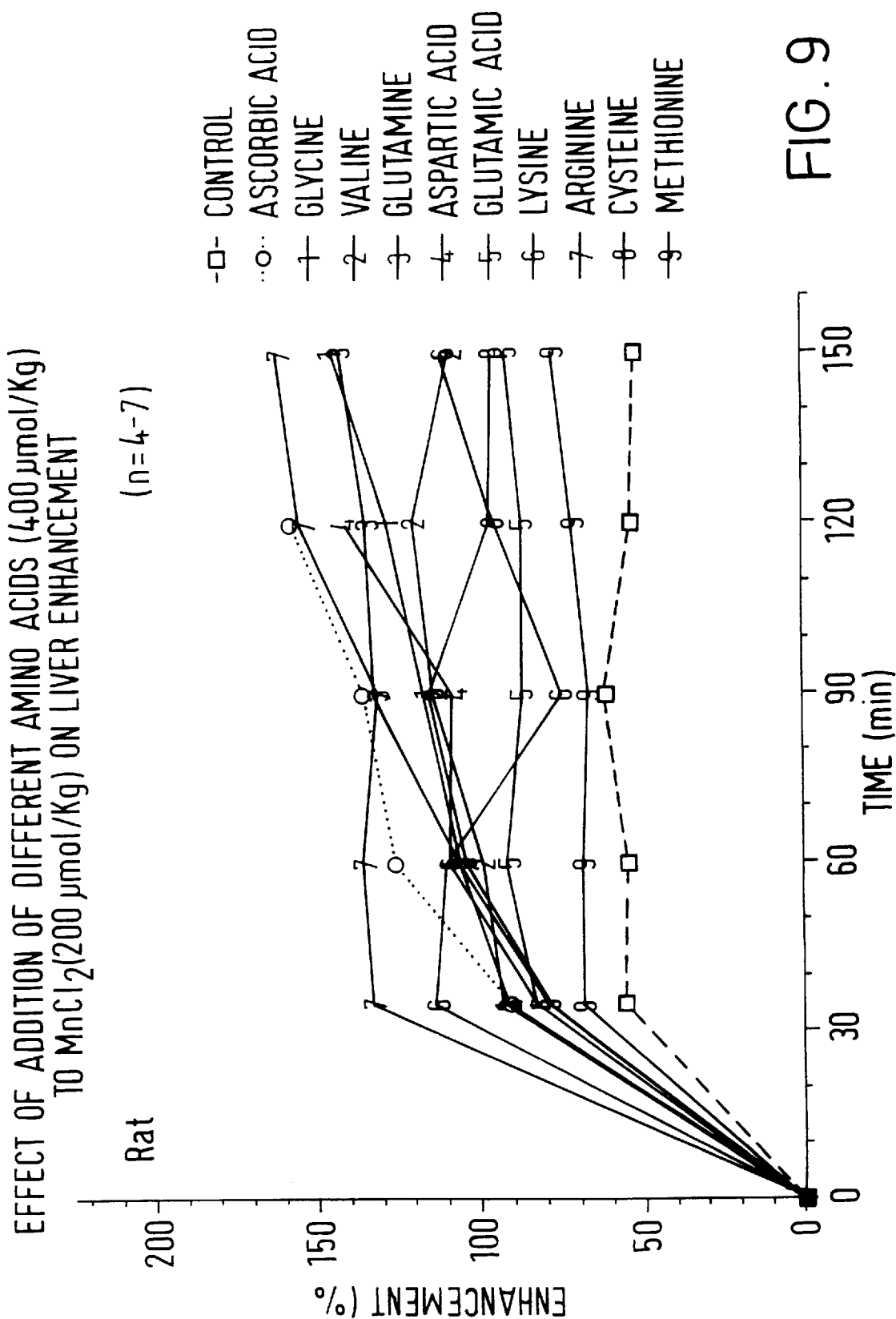
FIG. 9 is a graph illustrating the effect of the addition of different amino acids to $MnCl_2$ on liver enhancement.
Figure 10:
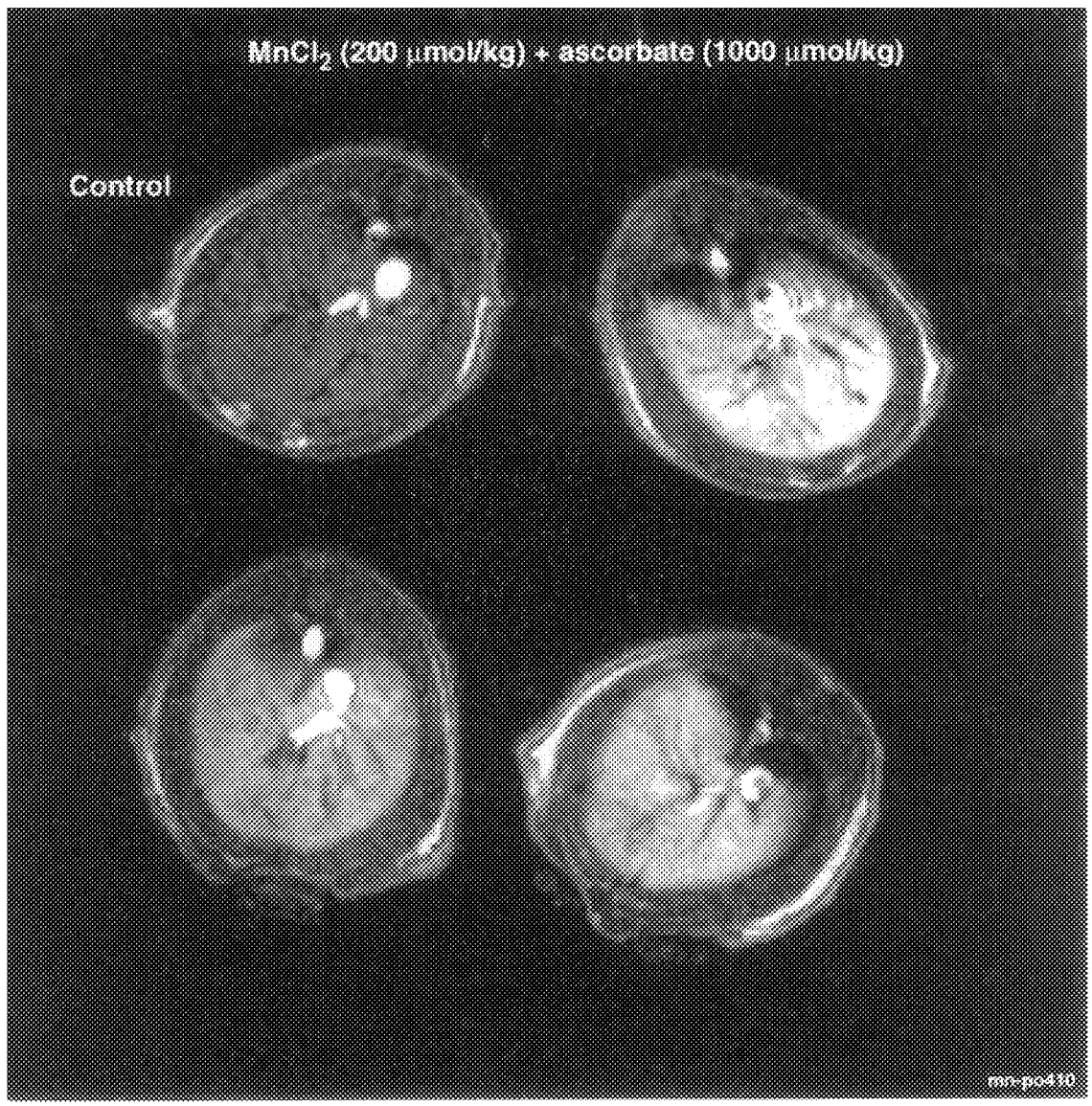
FIG. 10 illustrates transversal T1-weighted (SE 57/13; 2.4 T) liver images from a control rat and from three rats 2 hours after oral administration of 200 $\mu$mol/kg $MnCl_2$+1000 $\mu$mol/kg ascorbate. The signal intensity of the liver is substantially increased after gavage administration of $Mn^{2+}$ and ascorbate.
Figure 11:
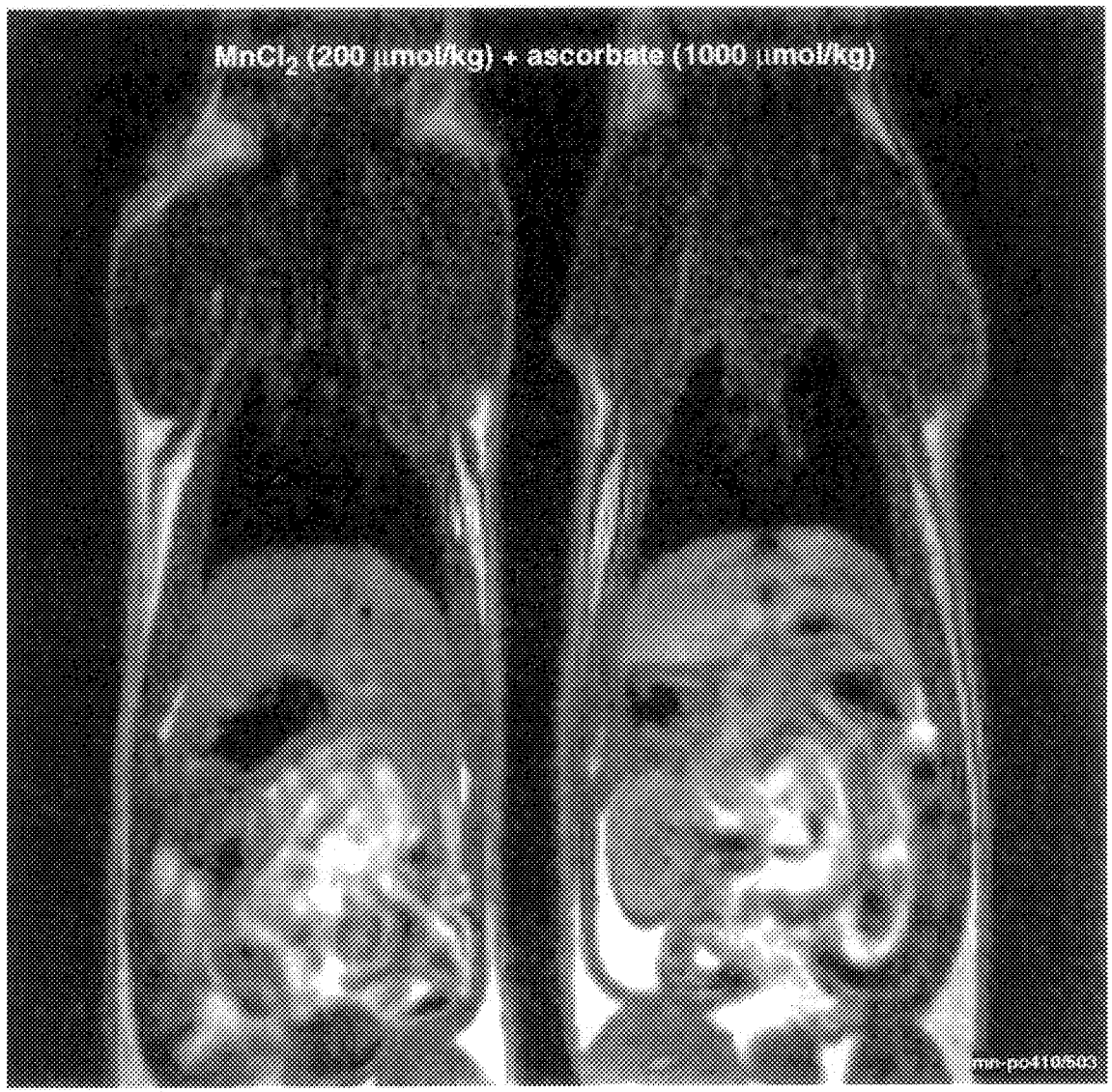
FIG. 11 illustrates coronal T1-weighted (SE 90/17; 2.4 T) liver images from two rats 2 hours after oral administration of 200 $\mu$mol/kg $MnCl_2$+1000 $\mu$mol/kg ascorbate. The signal intensity in the gastrointestinal lumen is reduced after administration of $Mn^{2+}$.
Figure 12:
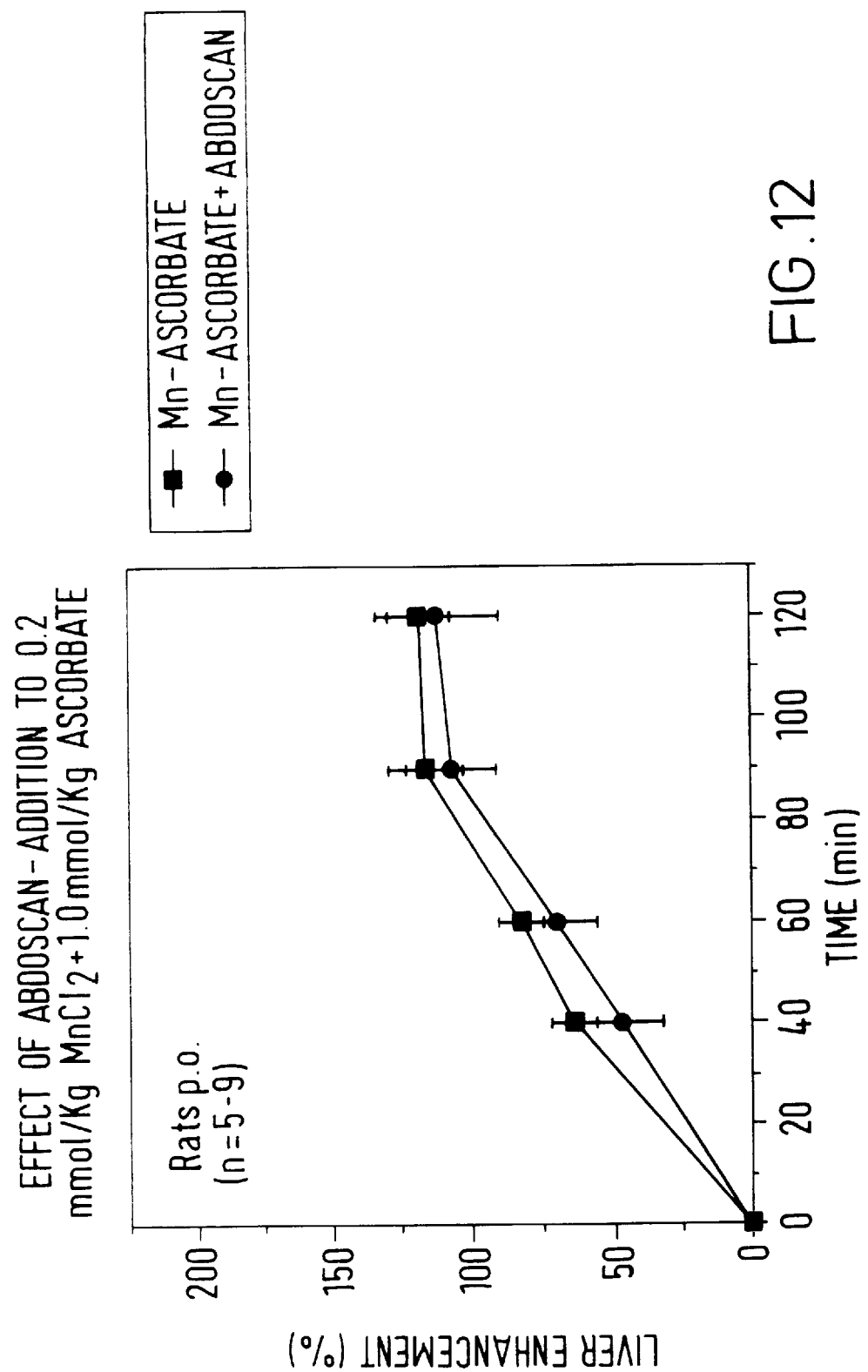
FIGS. 12 and 13 are graphs illustrating the effect of the addition of ABDOSCAN® to Mn-ascorbate on the enhancement of the liver.
Figure 13:
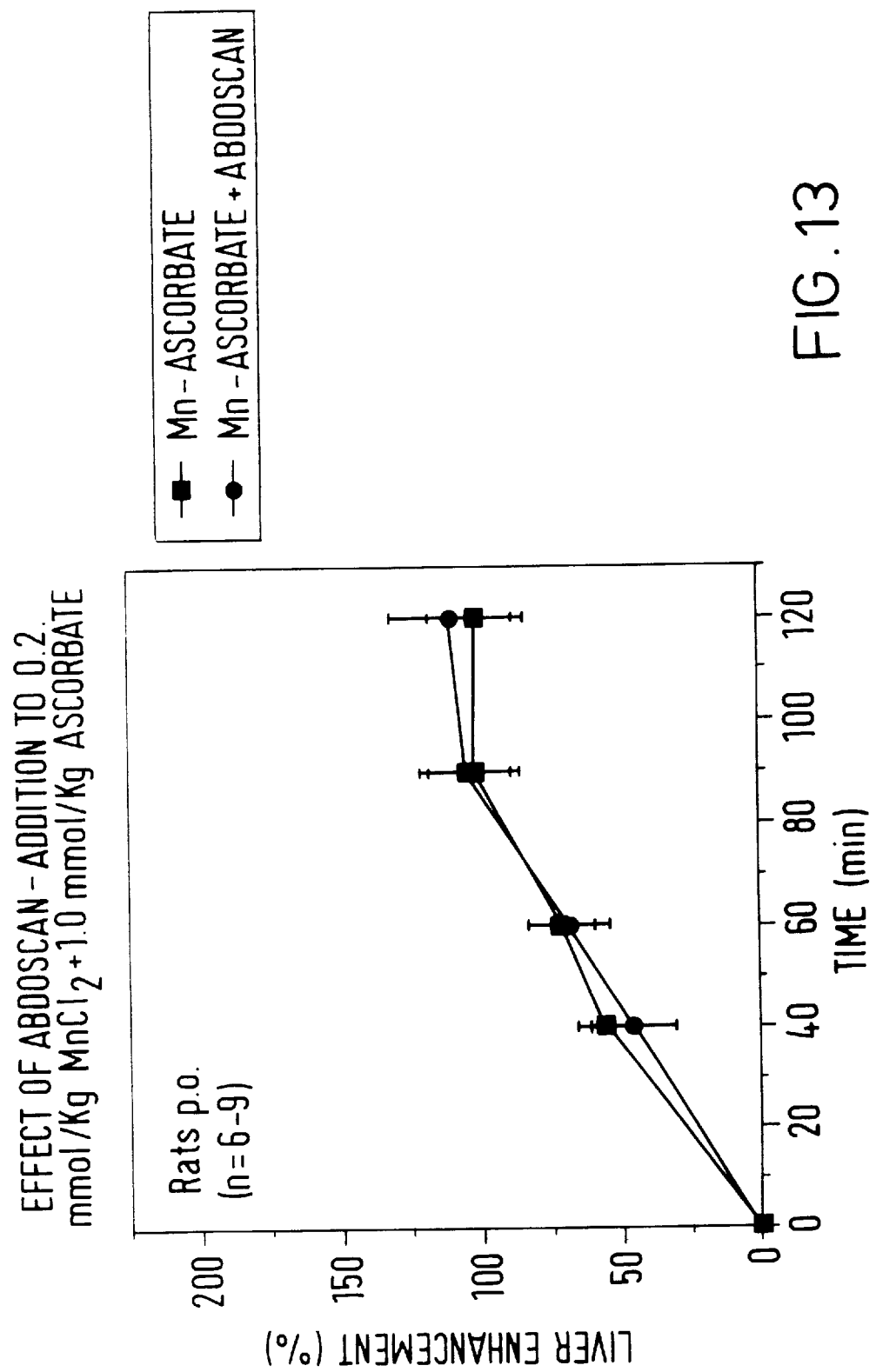
Figure 14:
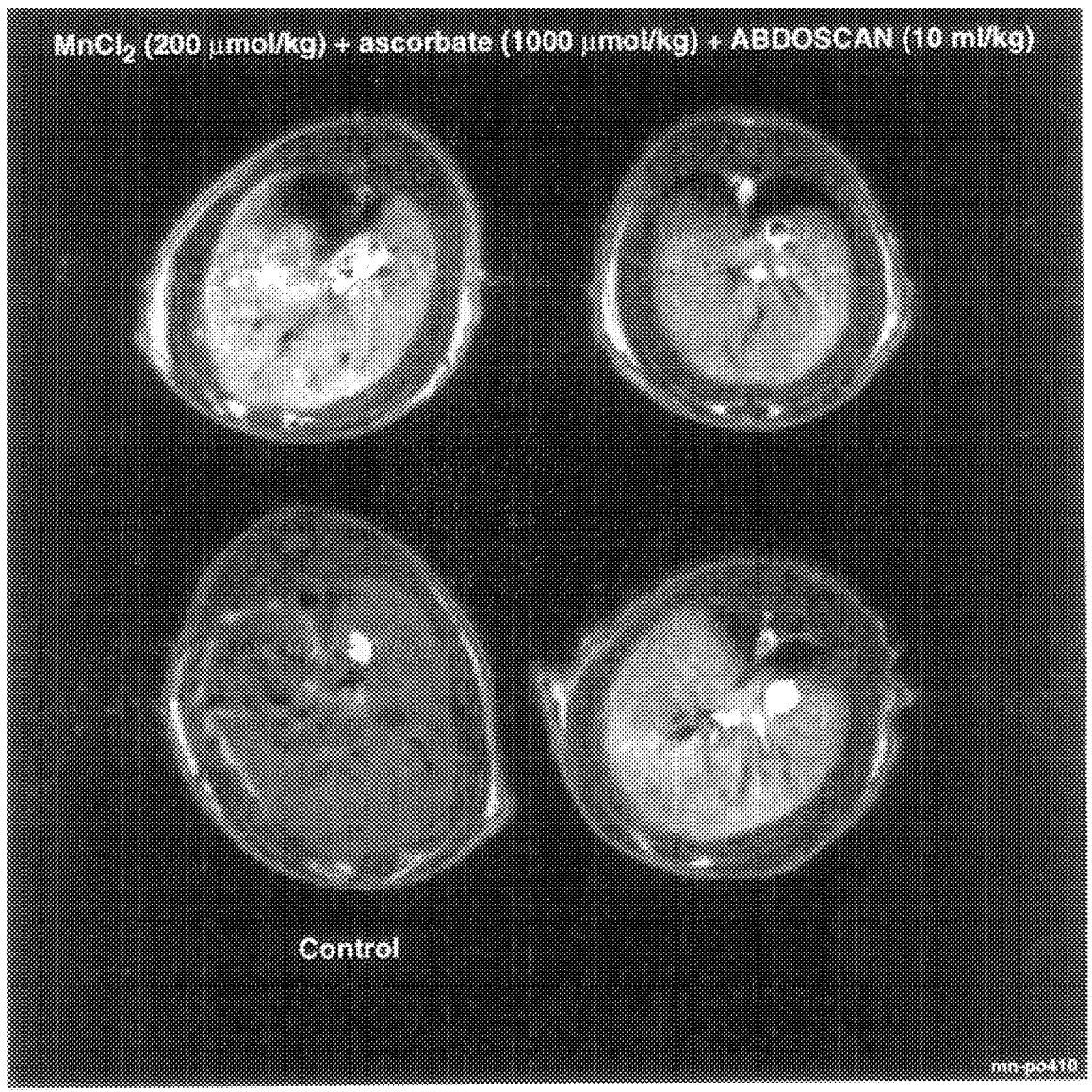
FIG. 14 illustrates transversal T1-weighted (SE 57/13; 2.4 T) liver images from a control rat and from three rats 2 hours after oral administration of 200 $\mu$mol/kg $MnCl_2$+1000 $\mu$mol/kg ascorbate+ABDOSCAN® (21 $\mu$mol/kg Fe). The addition of ABDOSCAN did not influence the signal intensity of the liver.
Figure 15:
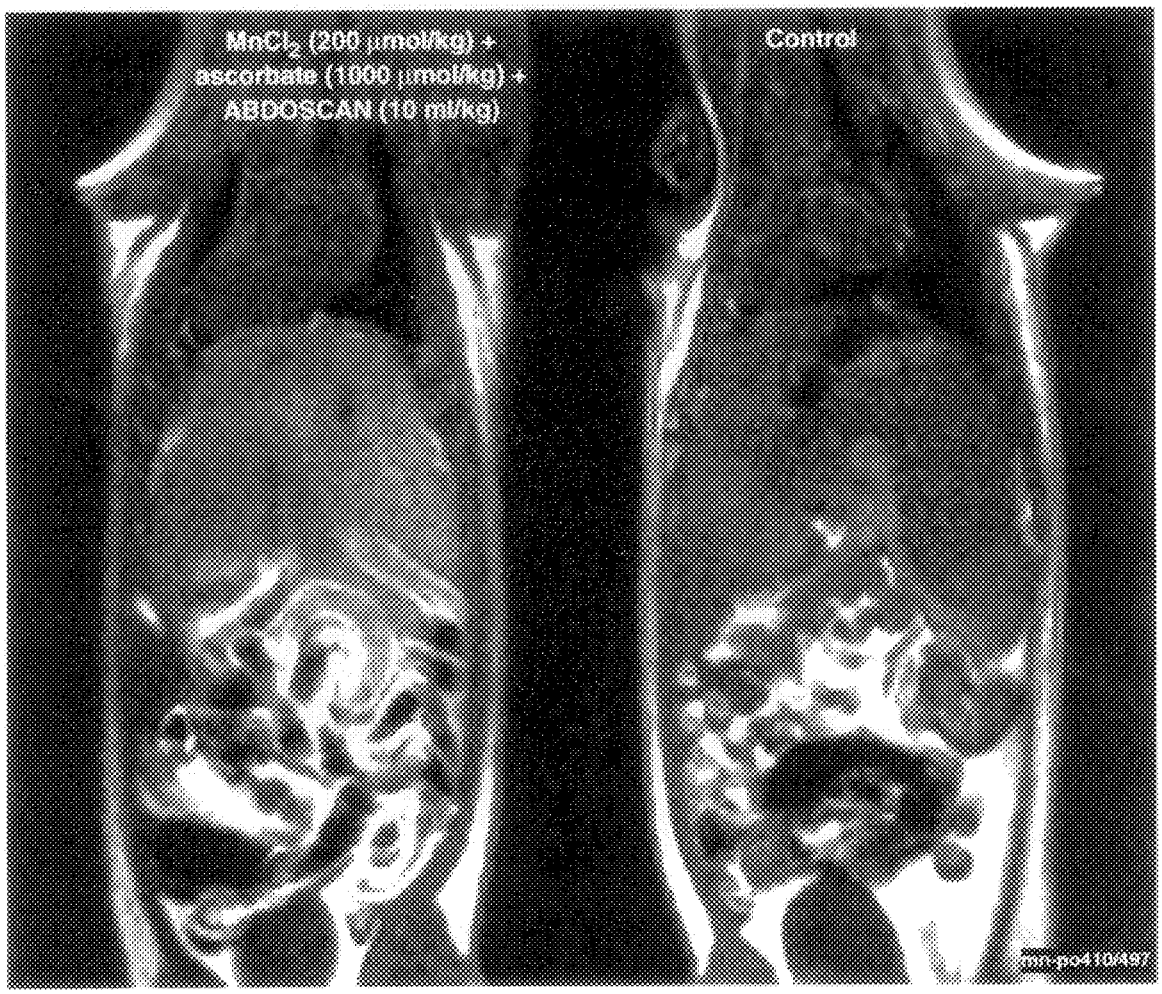
FIG. 15 illustrates coronal T1-weighted (SE 90/17; 2.4 T) liver images from a control rat and from a rat 2 hours after oral administration of 200 $\mu$mol/kg $MnCl_2$+1000 $\mu$mol/kg ascorbate+ABDOSCAN® (21 µmol/kg Fe). The signal intensity in the gastrointestinal lumen is markedly reduced after co-administration of $Mn^{2+}$ and ABDOSCAN.

For the measurement of the curves of FIGS. 12 and 13 the following materials were used:

| | | |
|---|---|---|
| MnCl₂ × 2H₂O | | 0.567 g |
| Asborbic acid | | 3.08 g |
| ABDOSCAN ® | | 23.4 mg Fe (one dose-package) |
| Water | ad | 200 ml |

Figure 16:
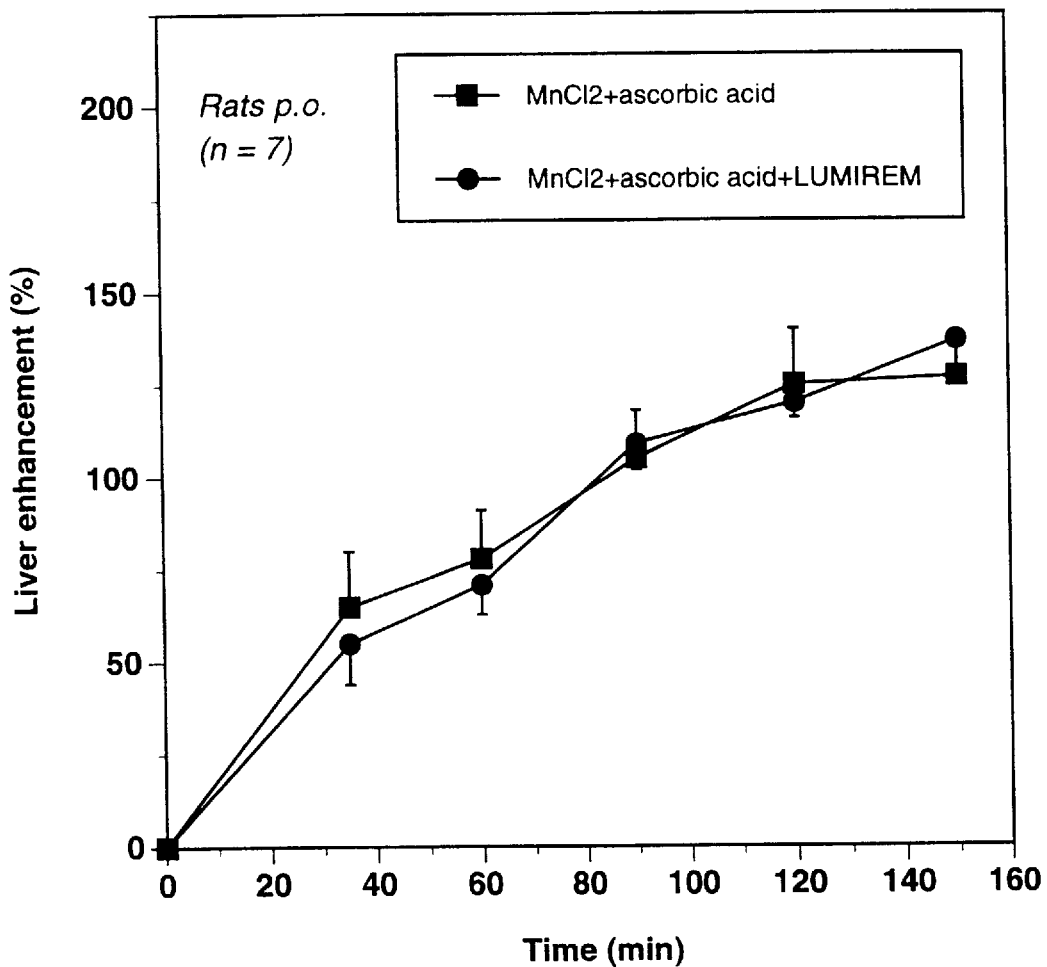
FIG. 16 is a graph illustrating the effect of the addition of LUMIREM to Mn-ascorbate on the enhancement of the liver.

For the measurement of the curves of FIG. 16 the following solutions were used:

| MnCl₂ (0.2 mmol/kg) + ascorbic acid | | |
|---|---|---|
| MnCl₂ × 2H₂O | | 0.065 g |
| Ascorbic acid | | 0.352 g |
| Distilled water | ad | 20 ml |

| MnCl₂ (0.2 mmol/kg) + ascorbic acid + LUMIREM | | |
|---|---|---|
| MnCl₂ × 2H₂O | | 0.065 g |
| Ascorbic acid | | 0.352 g |
| LUMIREM (0.175 mg Fe/ml) | ad | 20 ml |

In each case the rats were administered with 10 ml/kg of solution.

EXAMPLE 1

| Oral Composition | | |
|---|---|---|
| MnCl₂ × 2H₂O | | 6.48 g |
| Ascorbic acid | | 35.2 g |
| Water | ad | 1000 ml |

The manganese chloride and ascorbic acid are dissolved in sterile deionised water. The dose for a 70 kg adult human would be 350 ml, taken orally.

EXAMPLE 2

| Oral Composition | | |
|---|---|---|
| MnCl₂ × 2H₂O | | 6.48 g |
| Kojic acid | | 11.4 g |
| Water | ad | 1000 ml |

The manganese chloride and kojic acid are dissolved in sterile deionised water. The dose for a 70 kg adult human would be 350 ml, taken orally.

EXAMPLE 3

| Oral Composition | | |
|---|---|---|
| A. MnCl₂ × 2H₂O | | 13.0 g |
| Water | ad | 1000 ml |
| B. L-ascorbic acid 6-palmitate | | 66.4 g |
| Polyethylene glycol 300 | ad | 1000 ml |

The dose for a 70 kg adult human would be 175 ml of A and 175 ml of B, taken orally.

EXAMPLE 4

| Oral Composition | | |
|---|---|---|
| MnCl₂ × 2H₂O | | 0.567 g |
| Asborbic acid | | 3.08 g |
| ABDOSCAN ® | | 23.4 mg Fe |
| Water | ad | 200 ml |

The dose for a 70 kg adult human would be 4×200 ml, taken orally.

EXAMPLE 5

| Oral Composition - MnCl₂ (0.2 mmol/kg + vitamin D (0.4 mmol/kg) | | |
|---|---|---|
| A. MnCl₂ × 2H₂O | | 13.0 g |
| Water | ad | 1000 ml |
| B. Vitamin D | | 30.0 g |
| Polyethylene glycol 300 | ad | 1000 ml |

EXAMPLE 6

| Oral Composition | | |
|---|---|---|
| A. MnCl₂ × 2H₂O | | 2.27 g |
| Ascorbic acid | | 12.32 g |
| LUMIREM (0.175 mg Fe/ml) | ad | 300 ml |
| B. LUMIREM (0.175 mg Fe/ml) | | 300 ml |

The dose for a 70 kg adult human would be 1×300 ml of A followed by 2×300 ml of B, 30 and 60 minutes later.

We claim:

1. A contrast medium composition for oral and/or rectal administration comprising:
   (a) a first contrast agent comprising a physiologically tolerable manganese compound together with an uptake promoter, said first contrast agent having a manganese concentration of at least 0.3 mM or being in a dosage unit form containing at least 300 μmol manganese and having a molar ratio of manganese to uptake promoter of from 1:1 to 1:6, wherein the uptake promoter is selected from the group consisting of a physiologically tolerable reducing compound containing an α-hydroxy ketone group; a physiologically tolerable acid containing at least one moiety selected from the group consisting of an α-hydroxy, a β-hydroxy, an α-amino and a β-amino group, or a salt of said acid; and vitamin D; together with
   (b) a second contrast agent which has an opposing contrast effect to said first contrast agent.

2. A composition as claimed in claim 1 wherein the second contrast agent has a negative contrast effect.

3. A composition as claimed in claim 1 wherein the second contrast agent comprises a particulate ferromagnetic or superparamagnetic material.

4. A composition as claimed in claim 1 wherein the manganese compound is a chelate or a salt in which the manganese is present as Mn(II).

5. A composition as claimed in claim 1 wherein the reducing compound further contains an oxygen atom in a heterocyclic ring structure.

6. A composition as claimed in claim 1 wherein the uptake promoter is ascorbic acid.

7. A composition as claimed in claim 1 wherein the manganese compound comprises manganese ions and counterions thereto, the uptake promoter being present in whole or in part as said counterions.

8. A method of generating a magnetic resonance image of a human or non-human animal body, which method comprises orally and/or rectally administering into the gastrointestinal tract of a said body an effective amount of a composition as defined in claim 1 and generating a magnetic resonance image of the liver and abdomen of said body.

9. An MRI contrast agent kit comprising in a first container a first contrast agent comprising a physiologically tolerable manganese compound together with an uptake promoter, said first contrast agent having a manganese concentration of at least 0.3 mM or being in a dosage unit form containing at least 300 µmol manganese and having a molar ratio of manganese to uptake promoter of from 1:1 to 1:6, wherein the uptake promoter is selected from the group consisting of a physiologically tolerable reducing compound containing an α-hydroxy ketone group; a physiologically tolerable acid containing at least one moiety selected from the group consisting of an α-hydroxy, a β-hydroxy, an α-amino and a β-amino group, or a salt of said acid; and vitamin D; and in a second container a second contrast agent as defined in claim 3.

10. A method of generating a magnetic resonance image of a human or non-human animal body, which method comprises orally and/or rectally administering into the gastrointestinal tract of a said body an effective amount of a contrast medium composition and generating a magnetic resonance image of the liver and abdomen of said body, said contrast medium composition comprising:

(a) a first contrast agent comprising a physiologically tolerable manganese compound together with an uptake promoter, said first contrast agent having a manganese concentration of at least 0.3 mM or being in a dosage unit form containing at least 300 µmol manganese and having a molar ratio of manganese to uptake promoter of from 1:1 to 1:6, wherein the uptake promoter is selected from the group consisting of a physiologically tolerable reducing compound containing an α-hydroxy ketone group; a physiologically tolerable acid containing at least one moiety selected from the group consisting of an α-hydroxy, a β-hydroxy, an α-amino and a β-amino group, or a salt of said acid; and vitamin D; together with (b) a second contrast agent which has an opposing contrast effect to said first contrast agent.

11. A method as claimed in claim 10 wherein the second contrast agent has a negative contrast effect.

12. A method as claimed in claim 10 wherein the second contrast agent comprises a particulate ferromagnetic or superparamagnetic material.

13. A method as claimed in claim 10 wherein the manganese compound is a chelate or a salt in which the manganese is present as Mn(II).

14. A method as claimed in claim 10 wherein the reducing compound further contains an oxygen atom in a heterocyclic ring structure.

15. A method as claimed in claim 10 wherein the uptake promoter is ascorbic acid.

16. A method as claimed in claim 10 wherein the manganese compound comprises manganese ions and counterions thereto, the uptake promoter being present in whole or in part as said counterions.

17. A method as claimed in claim 10 wherein said image is generated using a single magnetic resonance imaging procedure.

* * * * *